United States Patent [19]

Terashima et al.

[11] Patent Number: 5,834,618
[45] Date of Patent: Nov. 10, 1998

[54] PROCESS FOR THE PREPARATION OF 3-AMINO-2-HYDROXY-4-PHENYLBUTYRONITRILE DERIVATIVES

[75] Inventors: Shiro Terashima, Tokyo; Norio Shibata, Kosugi-machi; Etsuko Itoh, Sagamihara, all of Japan

[73] Assignees: Kuraray Co., Ltd., Kurashiki; Sagami Chemical Research Center, Sagamihara, both of Japan

[21] Appl. No.: 994,448

[22] Filed: Dec. 19, 1997

[30] Foreign Application Priority Data

Dec. 20, 1996 [JP] Japan ................................... 8-340781
Sep. 22, 1997 [JP] Japan ................................... 9-256676

[51] Int. Cl.$^6$ ............................................. C07C 255/00
[52] U.S. Cl. ................................................... 558/408
[58] Field of Search ................................... 558/408

[56] References Cited

FOREIGN PATENT DOCUMENTS

WO 95/14653  6/1995  WIPO .

OTHER PUBLICATIONS

H. Suda et al, J. Antibiotics, vol. XXIX, No. 5, pp. 600–601 (1976).
M. T. Reetz et al, Tetrahedron Letters, vol. 29, No 27, pp. 3295–3298 (1988).
R. Herranz et al, Synthesis, pp. 703–706 (1989).
Tetsushi Saino, et al., The Journal of Antibiotics, vol. 40, No. 8, pp. 1165–1169, "Synthesis of $_p$-Hydroxyubenimex", 1987.

Derwent Abstract, AN—90–063689, JP 880165910, Jul. 5, 1998.

Chemical Abstracts, vol. 123, No. 3, p. 909, Jul. 17, 1995.

*Primary Examiner*—Johann Richter
*Assistant Examiner*—Joseph Murray
*Attorney, Agent, or Firm*—Oblon, Spivak, McClelland, Maier & Neustadt, P.C.

[57] ABSTRACT

3-Amino-2-hydroxy-4-phenylbutyronitrile derivatives represented by the formula (3) may be prepared by reacting an aminoaldehyde derivative represented by the formula (1) with a cyanohydrin derivative represented by the formula (2) in the presence of a metallic compound, base, or acid;

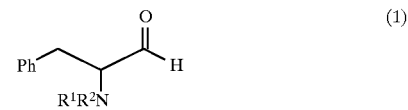

(1)

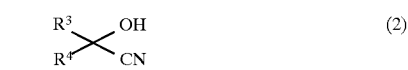

(2)

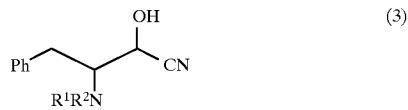

(3)

wherein $R^1$ and $R^2$ each independently represents a hydrogen atom or a protective group for an amino group, $R^3$ and $R^4$ each represents an alkyl or cycloalkyl group or $R^3$ and $R^4$ together form a tetramethylene or pentamethylene group.

20 Claims, No Drawings

PROCESS FOR THE PREPARATION OF 3-AMINO-2-HYDROXY-4-PHENYLBUTYRONITRILE DERIVATIVES

BACKGROUND OF THE INVENTION

1. Field of the Invention

The present invention relates to a process for the preparation of 3-amino-2-hydroxy-4-phenylbutyronitrile derivatives which are starting materials for the preparation of HIV protease inhibitors.

2. Discussion of the Background

3-Amino-2-hydroxy-4-phenylbutyronitrile derivatives represented by the following formula (3):

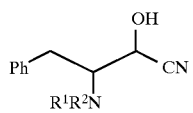

(3)

wherein $R^1$ and $R^2$ each independently represents a hydrogen atom or a protective group for an amino group, are known as starting materials for the synthesis of pharmaceuticals, particularly, as starting materials for the synthesis of HIV protease inhibitors. For example, KNI-272 (Japanese Patent Application Laid-Open No. HEI 5-170722, incorporated herein by reference) which is an anti-HIV agent is synthesized from 3-amino-2-hydroxy-4-phenylbutyric acid derived from a 3-amino-2-hydroxy-4-phenylbutyronitrile derivative represented by the above formula (3). 3-Dibenzylamino-1-isobutylamino-4-phenyl-2-butanol derived also from a 3-amino-2-hydroxy-4-phenylbutyronitrile derivative (3) is a starting material for the synthesis of SC-52151 (WO95/14653, incorporated herein by reference) which is an anti-HIV agent.

There are several processes for the synthesis of optically active 3-amino-2-hydroxy-4-phenylbutyronitrile derivatives known to date. One of the representative processes is a process [H. Suda, T. Takita, T. Aoyagi, and H. Umezawa, *J. Antibiotics*, 600 (1976)] in which a cyanohydrin derivative is prepared by the addition reaction of sodium cyanide or potassium cyanide to an (S)-2-amino-3-phenylpropanal derivative, but this process exhibits a generally low stereoselectivity. The stereoselective addition reaction of a cyano group by using trimethylsilyl cyanide has also been reported [WO 95/14653; M. T. Reetz, M. W. Drewes, K. Harms, and W. Reif, *Tetrahedron Lett.*, vol. 29, pp. 3295–3298 (1988)], but this process is not suited for industrial production because an expensive silyl compound is indispensable. In addition, a stereoselective addition reaction using triisobutyltin cyanide also has been reported [R. Herranz, J. C.-Pichel, and T. G.-Lopez, *Synthesis*, 703 (1989)] but it is also not suited for industrial production because of the use of a toxic tin compound.

Thus, there remains a need for an industrially feasible process for preparing a derivative of formula (3) in a high yield and with high stereoselectivity.

SUMMARY OF THE INVENTION

Accordingly it is one object of the present invention to provide a process which enables the industrial preparation of 3-amino-2-hydroxy-4-phenylbutyronitrile derivatives, which are starting materials for the preparation of HIV protease inhibitors, with high stereoselectivity.

This object has been achieved by the inventors' discovery that 3-amino-2-hydroxy-4-phenylbutyronitrile derivatives can be prepared with high stereoselectivity in a high yield by reacting a cyanohydrin derivative of a ketone typified by acetone cyanohydrin with a 2-amino-3-phenylpropanal derivative in the presence of a metallic compound, base, or acid as a catalyst, leading to the completion of the present invention.

Thus, the present invention provides a process for the preparation of a 3-amino-2-hydroxy-4-phenylbutyronitrile derivative represented by the following formula (3):

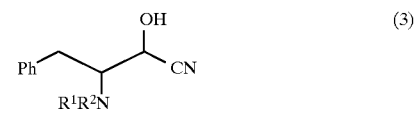

(3)

wherein $R^1$ and $R^2$ each independently represents a hydrogen atom or a protective group for an amino group, which comprises reacting an aminoaldehyde derivative represented by the formula (1):

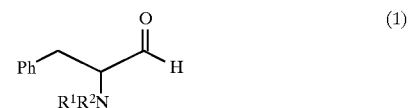

(1)

wherein $R^1$ and $R^2$ have the same meanings as defined above, with a cyanohydrin derivative represented by the following formula (2):

(2)

wherein $R^3$ and $R^4$ each independently represents an alkyl group or a cycloalkyl group, or $R^3$ and $R^4$ may be coupled together to form a tetramethylene or pentamethylene group, in the presence of a metallic compound, base, or acid. The 3-amino-2-hydroxy-4-phenylbutyronitrile derivative (3) may be either in the racemic form or in an optically active form.

DETAILED DESCRIPTION OF THE INVENTION

Examples of the protective group for an amino group usable in the present invention include acyl groups such as formyl, acetyl, trifluoroacetyl, benzoyl, pivaloyl, and phthaloyl; substituted or unsubstituted alkyloxycarbonyl groups such as benzyloxycarbonyl, t-butoxycarbonyl, isopropoxycarbonyl, ethoxycarbonyl, methoxycarbonyl, and allyloxycarbonyl; substituted alkyl groups such as benzyl, p-methoxybenzyl, and triphenylmethyl; sulfonyl groups such as p-toluenesulfonyl, benzenesulfonyl, and trifluoromethanesulfonyl; and silyl groups such as trimethylsilyl, t-butyldimethylsilyl, t-butyldiphenylsilyl, and triphenylsilyl. The above exemplified protective group can be introduced in a manner known per se in the art (refer to T. W. Greene, *Protective Groups in Organic Synthesis*, John-Wiley & Sons, New York, 1980, pp. 218–287).

As the alkyl group, either linear or branched one may be used. Examples include $C_{1-10}$ alkyl groups such as methyl, ethyl, propyl, isopropyl, butyl, isobutyl, t-butyl, pentyl, and hexyl. Examples of the cycloalkyl group include cyclopentyl and cyclohexyl.

Examples of the metallic compound usable in the present invention include easily available organic and inorganic metal compounds, e.g., aluminum compounds such as trimethylaluminum, triethylaluminum, diethylchloroaluminum, dichloroethylaluminum, and isobutylaluminum hydride; titanium compounds such as tetraisopropoxytitanium and titanium tetrachloride; and zinc compounds such as diethylzinc. Examples of the base include amines such as triethylamine, pyridine, diethylamine, and diisopropylethylamine; hydroxides of an alkali metal or alkaline earth metal such as sodium hydroxide, lithium hydroxide, potassium hydroxide, magnesium hydroxide, and barium hydroxide; and carbonates of an alkali metal or alkaline earth metal such as sodium carbonate, lithium carbonate, potassium carbonate, magnesium carbonate, and barium carbonate. Illustrative acids include organic and inorganic acids such as hydrochloric acid, sulfuric acid, and acetic acid; and Lewis acids such as zinc chloride, zinc iodide, ferric chloride, and tin chloride.

The 3-amino-2-hydroxy-4-phenylbutyronitrile derivative represented by the above formula (3) can be prepared in accordance with the following reaction scheme.

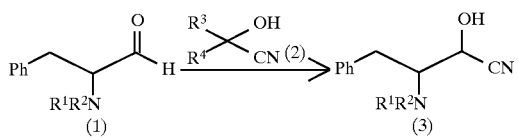

wherein $R^1$, $R^2$, $R^3$ and $R^4$ have the same meanings as defined above.

Specifically, a 3-amino-2-hydroxy-4-phenylbutyronitrile derivative (3) can be obtained with stereoselectivity by adding a cyanohydrin derivative (2) to an aminoaldehyde derivative (1) in the presence of a metallic compound, base, or acid. At this time, the use of an optically active aminoaldehyde derivative permits the preparation of an optically active 3-amino-2-hydroxy-4-phenylbutyronitrile derivative (see the Examples below).

The starting material aminoaldehyde derivative (1) including that in the R form and S form can be readily synthesized from readily available phenylalanine in a manner known per se in the art [for example, J. Jurczak and A. Golebiowski, *Chem. Rev.*, vol. 89, pp. 149–164 (1989); M. T. Reetz, M. W. Drewes, and A. Schmitz, *Angew. Chem. Int. Ed. Engl.*, vol. 26, pp. 1141–1143 (1987); J.-A. Fehrentz and B. Castro, *Synthesis*, 676–678 (1983); A. Abiko and S. Masamune, *Tetrahedron Lett.*, vol. 33, pp. 5517–5518 (1992); J. S. Ng, C. A. Przybyla, C. Liu, J. C. Yen, F. W. Muellner, and C. L. Weyker, *Tetrahedron*, vol. 51, pp. 6397–6410 (1995); P. O'Brien and S. Warren, *Tetrahedron Lett.*, vol. 37, pp. 4271–4274 (1996); P. L. Beaulieu and D. Wernic, *J. Org. Chem.*, vol. 61, pp. 3635–3645 (1996)].

Specific examples of the cyanohydrin derivative (2) include acetone cyanohydrin, butanone cyanohydrin, and cyclohexanone cyanohydrin. The cyanohydrin derivative (2) can be used in an amount of 1.0 to 20 equivalents, preferably 1.0 to 10 equivalents, based on the aminoaldehyde derivative (1).

As a reaction accelerator for use in the present invention which is selected from metallic compounds, acids, and bases, metallic compounds or Lewis acids, particularly, the former ones are preferred in the viewpoints of reaction efficiency, particularly stereoselectivity. Among the metallic compounds, organic aluminum compounds such as triethylaluminum and dichloroethylaluminum are used preferably. The reaction accelerator is used in an amount of 0.1 to 10 equivalents, preferably 1.0 to 2 equivalents, based on the aminoaldehyde derivative (1).

As a reaction solvent, any solvent can be used insofar as it does not react with raw materials under the reaction conditions. Illustrative of the reaction solvent include water, alcohols such as methanol, ethanol, isopropanol, and t-butanol, ethers such as diethyl ether, tetrahydrofuran (THF), dioxane, glyme, and diglyme; halogenated hydrocarbons such as methylene chloride, chloroform, 1,1,1-trichloroethane, and monochlorobenzene; hydrocarbons such as benzene, toluene, hexane, and pentane; fatty acid esters such as ethyl acetate and methyl acetate. It is also possible to use at least two of the above-exemplified solvents as a mixture. The reaction in methylene chloride is preferred.

The reaction can be effected at a temperature ranging from $-100°$ C. to the reflux temperature of the reaction solvent. It is preferred to carry out the reaction at $-20°$ to $25°$ C.

According to the process of the present invention, a 3-amino-2-hydroxy-4-phenylbutyronitrile derivative represented by the formula (3) having a configuration of (2S,3S) can be prepared with high selectivity compared with a 3-amino-2-hydroxy-4-phenylbutyronitrile derivative having a (2R,3S) configuration. The ratio of the (2S,3S) compound to the (2R,3S) compound can also be changed by selecting a protective group for the amino group.

A 3-amino-2-hydroxy-4-phenylbutyric acid derivative represented by the following formula (4):

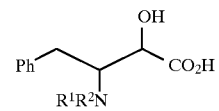

wherein $R^1$ and $R^2$ each independently represents a hydrogen atom or a protective group for an amino group, can be produced from a 3-amino-2-hydroxy-4-phenylbutyronitrile derivative represented by the formula (3) by subjecting it to the hydrolysis reaction of a nitrile group under acidic conditions (see the Reference Examples below).

The amino group of the compound (4) so obtained may then be deprotected, whereby 3-amino-2-hydroxy-4-phenylbutyric acid which is represented by the following formula (5):

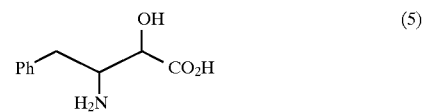

and is useful as a raw material for the synthesis of pharmaceuticals can be obtained (see the Reference Examples below).

Having generally described this invention, a further understanding can be obtained by reference to certain specific Examples and Reference Examples which are provided herein for purposes of illustration only and are not intended to be limiting unless otherwise specified.

EXAMPLES

Example 1

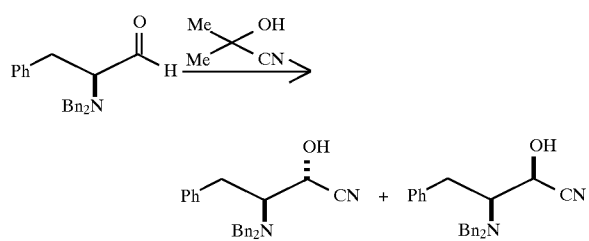

In an argon atmosphere, 0.230 mL (0.231 mmol) of a 0.99M hexane solution of trimethylaluminum was added to 1 mL of an anhydrous methylene chloride solution containing 50.7 mg (0.154 mmol) of (S)-2-N,N-dibenzylamino-3-phenylpropanal and 0.054 mL (0.551 mmol) of acetone cyanohydrin at −78° C., followed by stirring at −20° C. for 6 days. To the resulting solution 5 mL of a saturated ammonium chloride solution were added to terminate the reaction, followed by extraction with ethyl acetate (60 mL). The organic layer was washed with 30 mL of saturated saline, dried over anhydrous sodium sulfate, and concentrated under reduced pressure. The residue so obtained was purified by preparative thin-layer chromatography on silica gel (10% ethyl acetate/hexane), whereby 44.1 mg (80.4%) of 3-N,N-dibenzylamino-2-hydroxy-4-phenylbutyronitrile were obtained. The compound so obtained was a mixture (9:1) of (2S,3S)- and (2R,3S)-3-N,N-dibenzylamino-2-hydroxy-4-phenylbutyronitriles, and those two isomers can be separated by silica gel column chromatography or recrystallization.

(2S,3S)-3-N,N-Dibenzylamino-2-hydroxy-4-phenylbutyronitrile colorless crystals;
melting point: 97°–98° C. ($CH_2Cl_2$/hexane);
$[\alpha]_D^{20}$=+49.4°(c=1.01, $CHCl_3$);
IR (liquid membrane)/$cm^{-1}$ 3430 (OH), 2245 (CN);
$^1$H-NMR (400 MHz, $CDCl_3$): δ2.95 (1H, dd, J=10.5, 13.2 Hz, $CH_2Ph$), 3.21–3.26 (1H, m, CHN), 3.30 (1H, dd, J=4.5, 13.2 Hz, $CH_2Ph$), 3.53, 4.22 (4H, AB-q, J=13.2 Hz, Bn), 3.99 (1H, dd, J=5.5, 8.5 Hz, CHOH), 4.46 (1H, d, J=8.5 Hz, OH), 7.26 (15H, m, ArH);
MS (m/z) 357 ($MH^+$);
Anal. Calcd for $C_{24}H_{24}N_2O$: C 80.87; H 6.79; N 7.86, Found: C 81.01; H 6.98; N 7.81.

(2R,3S)-3-N,N-dibenzylamino-2-hydroxy-4-phenylbutyronitrile;

colorless oil;
$[\alpha]_D^{20}$=+47.9°(c=1.05, $CHCl_3$);
IR (liquid membrane)/$cm^{-1}$ 3430 (OH), 2255 (CN);
$^1$H-NMR (400 MHz, $CDCl_3$): δ2.99 (1H, dd, J=5.8, 14.1 Hz, $CH_2Ph$), 3.12 (1H, dd, J=8, 14.1 Hz, $CH_2Ph$), 3.33 (1H, ddd, J=5.8, 8, 8.5 Hz, CHN), 3.46, 3.85 (4H, AB-q, J=13.2 Hz, Bn), 3.89 (1H, brs, OH), 4.26 (1H, d, J=8.5 Hz, CHOH), 7.26 (15H, m, ArH);
MS(m/z) 357 ($MH^+$), 330 ($M^+$−CN), 265 ($M^+$−Bn).

Example 2

In an argon atmosphere, 0.23 mL (0.23 mmol) of a 0.99M hexane solution of trimethylaluminum was added to 1 mL of an anhydrous methylene chloride solution containing 50 mg (0.152 mmol) of (S)-2-N,N-dibenzylamino-3-phenylpropanal and 0.050 mL (0.547 mmol) of acetone cyanohydrin at −78° C., followed by stirring at −20° C. for 3 days. To the resulting solution, 5 mL of a saturated ammonium chloride solution were added to terminate the reaction, followed by extraction with ethyl acetate (60 mL). The organic layer was washed with 30 mL of saturated saline, dried over anhydrous sodium sulfate, and concentrated under reduced pressure. The residue so obtained was purified by preparative thin-layer chromatography on silica gel (10% ethyl acetate/hexane), whereby 40.3 mg (75%) of 3-N,N-dibenzylamino-2-hydroxy-4-phenylbutyronitrile were obtained. The compound so obtained was a mixture (13.3:1) of (2S,3S)- and (2R,3S)-3-N,N-dibenzylamino-2-hydroxy-4-phenylbutyronitriles, and those two isomers can be separated by silica gel column chromatography or recrystallization.

Example 3

In an argon atmosphere, 0.230 mL (0.228 mmol) of a 0.99M hexane solution of trimethylaluminum was added to 1 mL of an anhydrous methylene chloride solution containing 49.9 mg (0.152 mmol) of (S)-2-N,N-dibenzylamino-3-phenylpropanal and 0.050 mL (0.547 mmol) of acetone cyanohydrin under ice cooling, followed by stirring under the same conditions for 7 hours. To the resulting solution, 5 mL of a saturated ammonium chloride solution were added to terminate the reaction followed by extraction with ethyl acetate (60 mL). The organic layer was washed with 30 mL of saturated saline, dried over anhydrous sodium sulfate, and concentrated under reduced pressure. The residue so obtained was purified by preparative thin-layer chromatography on silica gel (10% ethyl acetate/hexane), whereby 54.1 mg (quant.) of 3-N,N-dibenzylamino-2-hydroxy-4-phenylbutyronitrile were obtained. The compound so obtained was a mixture (5.3:1) of (2S,3S)- and (2R,3S)-3-N,N-dibenzylamino-2-hydroxy-4-phenylbutyronitriles, and those two isomers can be separated by silica gel column chromatography or recrystallization.

Example 4

In an argon atmosphere, 0.25 mL (0.238 mmol) of a 0.96M hexane solution of dichloroethylaluminum was added to 1 mL of an anhydrous methylene chloride solution containing 52.5 mg (0.158 mmol) of (S)-2-N,N-dibenzylamino-3-phenylpropanal and 0.052 mL (0.569 mmol) of acetone cyanohydrin under ice cooling, followed by stirring at room temperature for 6 hours. To the resulting solution, 5 mL of a saturated ammonium chloride solution were added to terminate the reaction, followed by extraction with ethyl acetate (60 mL). The organic layer was washed with 30 mL of saturated saline, dried over anhydrous sodium sulfate, and concentrated under reduced pressure. The residue so obtained was purified by preparative thin-layer chromatography on silica gel (10% ethyl acetate/hexane), whereby 39.1 mg (70%) of 3-N,N-dibenzylamino-2-hydroxy-4-phenylbutyronitrile were obtained. The compound so obtained was a mixture (7.5:1) of (2S,3S)- and (2R,3S)-3-N,N-dibenzylamino-2-hydroxy-4-phenylbutyronitriles, and those two isomers can be separated by silica gel column chromatography or recrystallization.

Example 5

In an argon atmosphere, 0.050 mL (0.171 mmol) of tetraisopropoxytitanium was added to 1 mL of an anhydrous methylene chloride solution containing 56.2 mg (0.171 mmol) of (S)-2-N,N-dibenzylamino-3-phenylpropanal and 0.112 mL (1.225 mmol) of acetone cyanohydrin under ice cooling, followed by stirring at room temperature for 2 days. To the resulting solution, 5 mL of a saturated ammonium chloride solution were added to terminate the reaction, followed by extraction with ethyl acetate (60 mL). The organic layer was washed with 30 mL of saturated saline, dried over anhydrous sodium sulfate, and concentrated under reduced pressure. The residue so obtained was purified by preparative thin-layer chromatography on silica gel (10% ethyl acetate/hexane), whereby 56.2 mg (92%) of 3-N,N-dibenzylamino-2-hydroxy-4-phenylbutyronitrile were obtained. The compound so obtained was a mixture (3.4:1) of (2S,3S)- and (2R,3S)-3-N,N-dibenzylamino-2-hydroxy-4-phenylbutyronitriles, and those two isomers can be separated by silica gel column chromatography or recrystallization.

Example 6

In an argon atmosphere, 0.44 mL (0.44 mmol) of a 1.01M toluene solution of diisobutylaluminum hydride was added to 1 mL of an anhydrous methylene chloride solution containing 96.5 mg (0.293 mmol) of (S)-2-N,N-dibenzylamino-3-phenylpropanal and 0.096 mL (1.05 mmol) of acetone cyanohydrin under ice cooling, followed by stirring under the same conditions for 1 hour. To the resulting solution, 5 mL of a saturated ammonium chloride solution were added to terminate the reaction, followed by extraction with ethyl acetate (60 mL). The organic layer was washed with 30 mL of saturated saline, dried over anhydrous sodium sulfate, and concentrated under reduced pressure. The residue so obtained was purified by preparative thin-layer chromatography on silica gel (10% ethyl acetate/hexane), whereby 98 mg (94%) of 3-N,N-dibenzylamino-2-hydroxy-4-phenylbutyronitrile were obtained. The compound so obtained was a mixture (3:1) of (2S,3S)- and (2R,3S)-3-N,N-dibenzylamino-2-hydroxy-4-phenylbutyronitriles, and those two isomers can be separated by silica gel column chromatography of recrystallization.

Example 7

In an argon atmosphere, 0.26 mL (0.238 mmol) of a 0.92M hexane solution of triisobutylaluminum was added to 1 mL of an anhydrous methylene chloride solution containing 52.1 mg (0.158 mmol) of (S)-2-N,N-dibenzylamino-3-phenylpropanal and 0.052 mL (0.569 mmol) of acetone cyanohydrin under ice cooling, followed by stirring under the same conditions for 3 hours. To the resulting solution, 5 mL of a saturated ammonium chloride solution were added to terminate the reaction, followed by extraction with ethyl acetate (60 mL). The organic layer was washed with 30 mL of saturated saline, dried over anhydrous sodium sulfate, and concentrated under reduced pressure. The residue so obtained was purified by preparative thin-layer chromatography on silica gel (10% ethyl acetate/hexane), whereby 46.3 mg (82%) of 3-N,N-dibenzylamino-2-hydroxy-4-phenylbutyronitrile were obtained. The compound so obtained was a mixture (3:1) of (2S,3S)- and (2R,3S)-3-N,N-dibenzylamino-2-hydroxy-4-phenylbutyronitriles, and those two isomers can be separated by silica gel column chromatography or recrystallization.

Example 8

In an argon atmosphere, 26.6 mg (96%, 0.187 mmol) of zinc chloride were added to 1 mL of an anhydrous methylene chloride solution containing 41 mg (0.125 mmol) of (S)-2-N,N-dibenzylamino-3-phenylpropanal and 0.041 mL (0.449 mmol) of acetone cyanohydrin under ice cooling, followed by stirring at room temperature for 18 hours. To the resulting solution, 5 mL of a saturated ammonium chloride solution were added to terminate the reaction, followed by extraction with ethyl acetate (60 mL). The organic layer was washed with 30 mL of saturated saline, dried over anhydrous sodium sulfate, and concentrated under reduced pressure. The residue so obtained was purified by preparative thin-layer chromatography on silica gel (10% ethyl acetate/hexane), whereby 19.3 mg (43%) of 3-N,N-dibenzylamino-2-hydroxy-4-phenylbutyronitrile were obtained. The compound so obtained was a mixture (2:1) of (2S,3S)- and (2R,3S)-3-N,N-dibenzylamino-2-hydroxy-4-phenylbutyronitriles, and those two isomers can be separated by silica gel column chromatography or recrystallization.

Example 9

In an argon atmosphere, 1 mL of a saturated methanol solution of potassium carbonate was added to 51.7 mg (0.157 mmol) of (S)-2-N,N-dibenzylamino-3-phenylpropanal and 0.17 mL (1.86 mmol) of acetone cyanohydrin at room temperature, followed by stirring at room temperature for 5 hours. The reaction mixture was diluted with ethyl acetate (60 mL) and the diluted mixture was washed with 3% hydrochloric acid. The organic layer was washed with 30 mL of saturated saline, dried over anhydrous sodium sulfate, and concentrated under reduced pressure. The residue so obtained was purified by preparative thin-layer chromatography on silica gel (10% ethyl acetate/hexane), whereby 50.9 mg (91%) of 3-N,N-dibenzylamino-2-hydroxy-4-phenylbutyronitrile were obtained. The compound so obtained was a mixture (1:1) of (2S,3S)- and (2R,3S)-3-N,N-dibenzylamino-2-hydroxy-4-phenylbutyronitriles, and those two isomers can be separated by silica gel column chromatography or recrystallization.

Reference Example 1

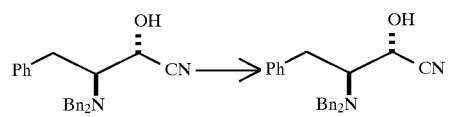

A solution of 199.4 mg (0.56 mmol) of (2S,3S)-3-N,N-dibenzylamino-2-hydroxy-4-phenylbutyronitrile in 20 mL of concentrated hydrochloric acid and 10 mL of water was stirred at 80° C. for a day. The solvent was removed by distillation, whereby (2S,3S)-3-N,N-dibenzylamino-2-hydroxy-4-phenylbutyric acid was obtained. The compound so obtained was used in the subsequent reaction (Reference Example 2) without purification.

Colorless oil;

$^1$H-NMR (400 MHz, CDCl$_3$): δ3.16 (1H, dd, J=9.6, 15.6 Hz, CH$_2$Ph), 3.56 (2H, m, CH$_2$Ph, CHN), 3.64, 4.14 (4H, AB-q, J=13.5 Hz, Bn), 4.15 (1H, m, CHOH), 7.38 (15H, m, ArH);

MS (m/z) 376 (MH$^+$).

Reference Example 2

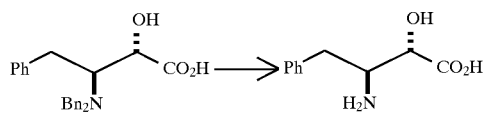

In a hydrogen atmosphere, 200 mg of 10% palladium/carbon were added to 40 mL of a solution of (2S,3S)-3-N,N-dibenzylamino-2-hydroxy-4-phenylbutyric acid (unpurified product), which had been obtained in the above reaction (Reference Example 1), in concentrated hydrochloric acid. The resulting mixture was stirred at room temperature overnight. The catalyst was then filtered off, followed by concentration under reduced pressure. The residue so obtained was purified by an ion exchange resin (Dowex 50W-X8), whereby 70.1 mg (64%, yield after two steps) of (2S,3S)-3-amino-2-hydroxy-4-phenylbutyric acid were obtained.

White crystals;

Melting point: 228°–233° C. (decomposed);

$[\alpha]_D^{20}$=−5.4°(c=0.37, 1N HCl);

IR (potassium bromide plate)/cm$^{-1}$ 3440 (br), 1615;

$^1$H-NMR (400 MHz, D$_2$O): δ2.85 (1H, dd, J=10.7, 14.5 Hz, CH$_2$Ph), 2.95 (1H, dd, J=4.1, 14.5 Hz, CH$_2$Ph), 3.83 (1H, ddd, J=3.6, 4.1, 10.7 Hz, CHN), 4.27 (1H, d, J=3.6 Hz, CHOH), 7.38 (5H, m, ArH);

MS(m/z) 196 (MH$^+$).

The preparation process of the present invention makes it possible to prepare a 3-amino-2-hydroxy-4-phenylbutyronitrile derivative, which is a starting material for the preparation of an HIV protease inhibitor, with high stereoselectivity in a high yield. In particular, it is possible to obtain an optically active substance having high optical purity conveniently.

This application is based on Japanese Patent Application Nos. 340781/1996, filed on Dec. 20, 1996, and 256676/1997, filed on Sep. 22, 1997, both of which are incorporated herein by reference in their entirety.

Obviously, numerous modifications and variations of the present invention are possible in light of the above teachings. It is therefore to be understood that, within the scope of the appended claims, the invention may be practiced otherwise than as specifically described herein.

What is claimed as new and is desired to be secured by Letters Patent of the United States is:

1. A process for the preparation of a compound of formula (3):

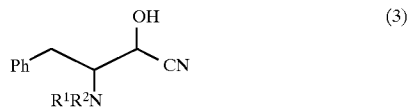

wherein R$^1$ and R$^2$ each independently represents a hydrogen atom or a protective group for an amino group, which comprises:

(i) reacting a compound of formula (1):

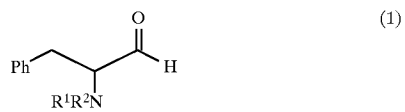

wherein R$^1$ and R$^2$ each independently represents a hydrogen atom or a protective group for an amino group, with a compound of formula (2):

wherein R$^3$ and R$^4$ each independently represents an alkyl group or a cycloalkyl group, or R$^3$ and R$^4$ together form a tetramethylene or pentamethylene group, in the presence of a metallic compound, base, or acid.

2. The process of claim 1, wherein R$^1$ and R$^2$ each independently is selected from the group consisting of hydrogen, formyl, acetyl, trifluoroacetyl, benzoyl, pivaloyl, phthaloyl, benzyloxycarbonyl, t-butoxycarbonyl, isopropoxycarbonyl, ethoxycarbonyl, methoxycarbonyl, allyloxycarbonyl, benzyl, p-methoxybenzyl, triphenylmethyl, p-toluenesulfonyl, benzenesulfonyl, trifluoromethanesulfonyl, trimethylsilyl, t-butyldimethylsilyl, t-butyldiphenylsilyl, and triphenylsilyl.

3. The process of claim 1, wherein R$^3$ and R$^4$ each independently is selected from the group consisting of methyl, ethyl, propyl, isopropyl, butyl, isobutyl, t-butyl, pentyl, hexyl, cyclopentyl, and cyclohexyl.

4. The process of claim 1, wherein said reacting is carried out in the presence of a metallic compound.

5. The process of claim 4, wherein said metallic compound is selected from the group consisting of trimethylaluminum, triethylaluminum, diethylchloroaluminum, dichloroethylaluminum, isobutylaluminum hydride, tetraisopropoxytitanium, titanium tetrachloride, and diethylzinc.

6. The process of claim 1, wherein said reacting is carried out in the presence of a base.

7. The process of claim 6, wherein said base is selected from the group consisting of triethylamine, pyridine, diethylamine, diisopropylethylamine, sodium hydroxide, lithium hydroxide, potassium hydroxide, magnesium hydroxide, barium hydroxide, sodium carbonate, lithium carbonate, potassium carbonate, magnesium carbonate, and barium carbonate.

8. The process of claim 1, wherein said reacting is carried out in the presence of an acid.

9. The process of claim 8, wherein said acid is selected from the group consisting of of hydrochloric acid, sulfuric acid, acetic acid, zinc chloride, zinc iodide, ferric chloride, and tin chloride.

10. The process of claim 1, wherein R$^1$ and R$^2$ each are benzyl.

11. The process of claim 1, wherein said compound of formula (2) is selected from the group consisting of acetone cyanohydrin, butanone cyanohydrin, and cyclohexanone cyanohydrin.

12. The process of claim 1, wherein said reacting is carried out in a solvent selected from the group consisting of water, methanol, ethanol, isopropanol, t-butanol, diethyl ether, tetrahydrofuran, dioxane, glyme, diglyme, methylene chloride, chloroform, 1,1,1-trichloroethane, monochlorobenzene, benzene, toluene, hexane, pentane, ethyl acetate, methyl acetate, and mixtures thereof.

13. The process of claim 1, wherein said compound of formula (1) and said compound of formula (2) are reacted in relative amounts of 1.0 to 20 equivalents of said compound of formula (2), per equivalent of said compound of formula (1).

14. The process of claim 1, wherein said compound of formula (1) and said compound of formula (2) are reacted in the presence of 0.1 to 10 equivalents of said metallic compound, base, or acid, per equivalent of said compound of formula (1).

15. A process for the preparation of a compound of formula (5),

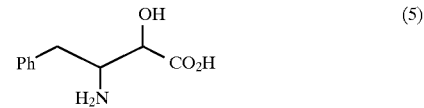

comprising:

(i) reacting a compound of formula (1):

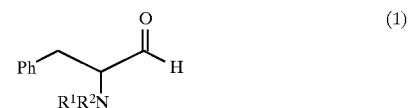

wherein R$^1$ and R$^2$ each independently represents a hydrogen atom or a protective group for an amino group, with a compound of formula (2):

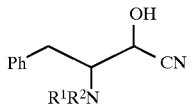  (2)

wherein $R^3$ and $R^4$ each independently represents an alkyl group or a cycloalkyl group, or $R^3$ and $R^4$ together form a tetramethylene or pentamethylene group, in the presence of a metallic compound, base, or acid, to obtain a compound of formula (3)

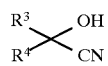  (3)

wherein $R^1$ and $R^2$ each independently represents a hydrogen atom or a protective group for an amino group; and (ii) hydrolyzing said compound of formula (3), followed by removal of $R^1$ and $R^2$, if necessary, to obtain said compound of formula (5).

16. The process of claim 15, wherein $R^1$ and $R^2$ each independently is selected from the group consisting of hydrogen, formyl, acetyl, trifluoroacetyl, benzoyl, pivaloyl, phthaloyl, benzyloxycarbonyl, t-butoxycarbonyl, isopropoxycarbonyl, ethoxycarbonyl, methoxycarbonyl, allyloxycarbonyl, benzyl, p-methoxybenzyl, triphenylmethyl, p-toluenesulfonyl, benzenesulfonyl, trifluoromethanesulfonyl, trimethylsilyl, t-butyldimethylsilyl, t-butyldiphenylsilyl, and triphenylsilyl;

$R^3$ and $R^4$ each independently is selected from the group consisting of methyl, ethyl, propyl, isopropyl, butyl, isobutyl, t-butyl, pentyl, hexyl, cyclopentyl, and cyclohexyl;

said reacting is carried out in the presence of a metallic compound selected from the group consisting of trimethylaluminum, triethylaluminum, diethylchloroaluminum, dichloroethylaluminum, isobutylaluminum hydride, tetraisopropoxytitanium, titanium tetrachloride, and diethylzinc;

said reacting is carried out in a solvent selected from the group consisting of water, methanol, ethanol, isopropanol, t-butanol, diethyl ether, tetrahydrofuran, dioxane, glyme, diglyme, methylene chloride, chloroform, 1,1,1-trichloroethane, monochlorobenzene, benzene, toluene, hexane, pentane, ethyl acetate, methyl acetate, and mixtures thereof;

said compound of formula (1) and said compound of formula (2) are reacted in relative amounts of 1.0 to 20 equivalents of said compound of formula (2), per equivalent of said compound of formula (1); and said compound of formula (1) and said compound of formula (2) are reacted in the presence of 0.1 to 10 equivalents of said metallic compound, per equivalent of said compound of formula (1).

17. In a process for preparing KNI-272, comprising converting 3-amino-2-hydroxy-4-phenylbutyric acid to KNI-272, the improvement being that said 3-amino-2-hydroxy-4-phenylbutyric acid is prepared by a process comprising:

(i) reacting a compound of formula (1):

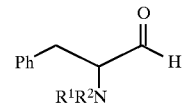  (1)

wherein $R^1$ and $R^2$ each independently represents a hydrogen atom or a protective group for an amino group, with a compound of formula (2):

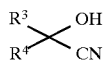  (2)

wherein $R^3$ and $R^4$ each independently represents an alkyl group or a cycloalkyl group, or $R^3$ and $R^4$ together form a tetramethylene or pentamethylene group, in the presence of a metallic compound, base, or acid, to obtain a compound of formula (3)

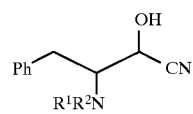  (3)

wherein $R^1$ and $R^2$ each independently represents a hydrogen atom or a protective group for an amino group;

(ii) hydrolyzing said compound of formula (3), followed by removal of $R^1$ and $R^2$, if necessary, to obtain said 3-amino-2-hydroxy-4-phenylbutyric acid; and (iii) converting said 3-amino-2-hydroxy-4-phenylbutyric acid to said KNI-272.

18. The process of claim 17, wherein $R^1$ and $R^2$ each independently is selected from the group consisting of hydrogen, formyl, acetyl, trifluoroacetyl, benzoyl, pivaloyl, phthaloyl, benzyloxycarbonyl, t-butoxycarbonyl, isopropoxycarbonyl, ethoxycarbonyl, methoxycarbonyl, allyloxycarbonyl, benzyl, p-methoxybenzyl, triphenylmethyl, p-toluenesulfonyl, benzenesulfonyl, trifluoromethanesulfonyl, trimethylsilyl, t-butyldimethylsilyl, t-butyldiphenylsilyl, and triphenylsilyl;

$R^3$ and $R^4$ each independently is selected from the group consisting of methyl, ethyl, propyl, isopropyl, butyl, isobutyl, t-butyl, pentyl, hexyl, cyclopentyl, and cyclohexyl;

said reacting is carried out in the presence of a metallic compound selected from the group consisting of trimethylaluminum, triethylaluminum, diethylchloroaluminum, dichloroethylaluminum, isobutylaluminum hydride, tetraisopropoxytitanium, titanium tetrachloride, and diethylzinc;

said reacting is carried out in a solvent selected from the group consisting of water, methanol, ethanol, isopropanol, t-butanol, diethyl ether, tetrahydrofuran, dioxane, glyme, diglyme, methylene chloride, chloroform, 1,1,1-trichloroethane, monochlorobenzene, benzene, toluene, hexane, pentane, ethyl acetate, methyl acetate, and mixtures thereof, said compound of formula (I) and said compound of formula (2) are reacted in relative amounts of 1.0 to 20 equivalents of said compound of formula (2), per equivalent of said compound of formula (1); and said compound of formula (1) and said compound of formula (2) are reacted in the presence of 0.1 to 10 equivalents of said metallic compound, per equivalent of said compound of formula (1).

19. In a process for preparing SC-52151, comprising converting 3-dibenzylamino-1-isobutylamino-4-phenyl-2-butanol to SC-52151, the improvement being that said 3-dibenzylamino-1-isobutylamino-4-phenyl-2-butanol is prepared from a compound of formula (3):

wherein $R^1$ and $R^2$ each independently represents a hydrogen atom or a protective group for an amino group, and said compound of formula (3) is prepared by a process which comprises:

(i) reacting a compound of formula (1):

wherein $R^1$ and $R^2$ each independently represents a hydrogen atom or a protective group for an amino group, with a compound of formula (2):

wherein $R^3$ and $R^4$ each independently represents an alkyl group or a cycloalkyl group, or $R^3$ and $R^4$ together form a tetramethylene or pentamethylene group, in the presence of metallic compound, base, or acid, to obtain said compound of formula (3);

(ii) converting said compound of formula (3) to said 3-dibenzylamino-1-isobutylamino-4-phenyl-2-butanol; and (iii) converting said 3-dibenzylamino-1-isobutylamino-4-phenyl-2-butanol to said SC-52151.

20. The process of claim 19, wherein $R^1$ and $R^2$ each independently is selected from the group consisting of hydrogen, formyl, acetyl, trifluoroacetyl, benzoyl, pivaloyl, phthaloyl, benzyloxycarbonyl, t-butoxycarbonyl, isopropoxycarbonyl, ethoxycarbonyl, methoxycarbonyl, allyloxycarbonyl, benzyl, p-methoxybenzyl, triphenylmethyl, p-toluenesulfonyl, benzenesulfonyl, trifluoromethanesulfonyl, trimethylsilyl, t-butyldimethylsilyl, t-butyldiphenylsilyl, and triphenylsilyl;

$R^3$ and $R^4$ each independently is selected from the group consisting of methyl, ethyl, propyl, isopropyl, butyl, isobutyl, t-butyl, pentyl, hexyl, cyclopentyl, and cyclohexyl;

said reacting is carried out in the presence of a metallic compound selected from the group consisting of trimethylaluminum, triethylaluminum, diethylchloroaluminum, dichloroethylaluminum, isobutylaluminum hydride, tetraisopropoxytitanium, titanium tetrachloride, and diethylzinc;

said reacting is carried out in a solvent selected from the group consisting of water, methanol, ethanol, isopropanol, t-butanol, diethyl ether, tetrahydrofuran, dioxane, glyme, diglyme, methylene chloride, chloroform, 1,1,1-trichloroethane, monochlorobenzene, benzene, toluene, hexane, pentane, ethyl acetate, methyl acetate, and mixtures thereof;

said compound of formula (1) and said compound of formula (2) are reacted in relative amounts of 1.0 to 20 equivalents of said compound of formula (2), per equivalent of said compound of formula (1); and said compound of formula (1) and said compound of formula (2) are reacted in the presence of 0.1 to 10 equivalents of said metallic compound, per equivalent of said compound of formula (1).

* * * * *